(12) United States Patent
Light

(10) Patent No.: US 10,499,945 B2
(45) Date of Patent: Dec. 10, 2019

(54) SURGICAL SCRAPER WITH REMOVEABLE BLADE AND CONTAINER THEREFOR

(71) Applicant: Kenneth I. Light, San Francisco, CA (US)

(72) Inventor: Kenneth I. Light, San Francisco, CA (US)

( * ) Notice: Subject to any disclaimer, the term of this patent is extended or adjusted under 35 U.S.C. 154(b) by 317 days.

(21) Appl. No.: 15/442,595

(22) Filed: Feb. 24, 2017

(65) Prior Publication Data

US 2018/0242994 A1    Aug. 30, 2018

(51) Int. Cl.
*A61B 17/3205* (2006.01)
*A61B 17/32* (2006.01)
*A61B 17/00* (2006.01)

(52) U.S. Cl.
CPC ............ *A61B 17/3205* (2013.01); *A61B 2017/00473* (2013.01); *A61B 2017/320008* (2013.01)

(58) Field of Classification Search
CPC .............. A61B 17/32; A61B 17/3205; A61B 17/320708; A61B 17/3209; A61B 17/3211; A61B 17/3213; A61B 17/3217; A61B 2017/0046; A61B 2017/00473; A61B 2017/320008; B23D 71/04; B23D 71/06; B23D 71/08; A47L 13/02; A47L 13/08
See application file for complete search history.

(56) References Cited

U.S. PATENT DOCUMENTS

| | | | |
|---|---|---|---|
| 1,754,650 A * | 4/1930 | Nils Seaholm | A61B 17/3213 30/337 |
| 2,494,455 A | 1/1950 | Soldani | |
| 5,001,796 A | 3/1991 | Desjardins | |
| 2003/0110641 A1* | 6/2003 | Gringer | A47L 13/022 30/169 |
| 2006/0212058 A1* | 9/2006 | Djordjevic | A61B 17/3213 606/167 |
| 2009/0112240 A1 | 4/2009 | Slaughter et al. | |
| 2010/0168773 A1 | 7/2010 | Funderburk | |

* cited by examiner

*Primary Examiner* — Robert A Lynch
(74) *Attorney, Agent, or Firm* — Corner Counsel, LLC

(57) ABSTRACT

A scraper is provided having at least a portion of a fastener thereon. A blade is removably attachable to the distal end of the scraper through this fastener. The blade includes a cutting edge extending beyond portions of the distal end so that the cutting edge of the blade can be used when the blade is attached to the scraper. One form of fastener includes a pin and a hole, both on the distal end of the scraper. The blade is provided with a yoke that engages the pin, and a stud which passes through the hole, so that the blade is secured to the distal end of the scraper. A container is also disclosed with a lower tray and cover tray configured to hold multiple scrapers therein.

7 Claims, 5 Drawing Sheets

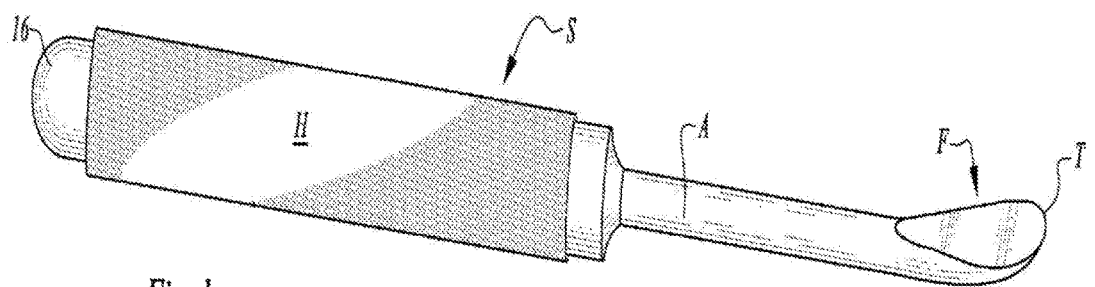

SURGICAL SCRAPER WITH REMOVEABLE BLADE AND CONTAINER THEREFOR

FIELD OF THE INVENTION

The following invention relates to scrapers such as surgical scrapers with an elongate handle extending to a distal tip sharpened to cut and scrape. More particularly, this invention relates to such elongated scrapers which also have a removable plate at the distal end of the scraper.

BACKGROUND OF THE INVENTION

Surgical scrapers currently in use are one piece devices which are provided to surgeons by hospitals as common surgical facility tools. Surgical scrapers are utilized to separate tissue (e.g. muscle, etc.) from bone, such as when performing various spinal fusion procedures where the bone must be exposed for effective operation on the vertebra. One such scraper is known in the art as a "Cobb Elevator." Such a scraper has a rigid elongate body extending from a handle at a proximal end to a distal end, spaced from the handle by an arm. The distal end has a tip that is sharpened to do the scraping.

To function properly, a surgical scraper must have a sharp scraping edge at its tip. In use, this sharp edge wears off quickly. Because the surgeon typically does not have control over when a scraper gets sharpened, or how well it gets sharpened, when a surgeon is handed a sterilized scraper during surgery, the surgeon is often required to then use that surgical scraper which has either not been properly sharpened and/or has become dull or damaged (e.g. notched) since its last sharpening. Accordingly, a need exists for a surgical scraper which has a replaceable blade. Such a surgical scraper would always have a new (or newly refurbished) sharp blade available for use, which blade would be typically disposed of after each use, but which could be separately sterilizable, refurbished and reused.

SUMMARY OF THE INVENTION

This invention is a scraper which includes two parts. The first part is a handle. A most proximal end of the handle preferably includes some form of grip and is configured to be held by a user. The distal end of this handle flares to a greater width which comprises the handle head. A distal end of this handle portion is modified to include at least part of a fastener, to hold a blade releasably thereto. In an exemplary embodiment, this fastener includes a pin and a hole. The hole is closest to a distal end of the scraper's distal end, with the pin closer to the handle than the hole. In other embodiments, the hole is closest to the handle, with the pin closer to the distal end of the scraper distal end than to the hole. The distal end of the handle between the hole and the locating pin preferably has a slight concave form. The hole is preferably substantially round, however other shapes can be used. The locating pin is preferably press-fit into a locating pin receiving bore formed at the desired location in the handle slightly further from the distal end of the handle than the hole. In other embodiments, the locating pin receiving bore is formed at a location in the handle closer to the distal end of the handle than the hole. This pin has a cap with a greater diameter than a post thereof, and with the post going into this locating pin receiving bore.

A removable blade attaches to the handle through the hole and locating pin. The blade is a thin piece of rigid hard material, such as for example, stainless steel or other metal, and preferably is a material which is resilient so that it can flex somewhat and snap back to an original shape. This blade has a slight curvature thereto and may exhibit slightly more curvature than the distal end of the handle adjacent the hole and locating pin. The blade may have a peripheral contour similar to a peripheral contour of the distal end of the handle.

The edge of the blade is sharp, having been sharpened down to a cutting edge at a distal side thereof. The blade is sized to extend slightly beyond the distal end of the handle when attached to the handle. The blade preferably includes two fastener portions to facilitate its attachment to the handle. First, the blade has a stud sized to fit into the hole adjacent the distal end of the handle. The blade also has a yoke spaced from the stud at a distance, causing the yoke to fit under the cap of the locating pin, particularly at a slot in a midpoint of the yoke. The yoke portion of the blade is preferably slightly bent to enhance the concave form of the blade. Thus, when the yoke of the blade is placed under the cap of the locating pin, and the blade is pressed down until its alignment stud passes into the hole in the distal end of the handle, the blade is captured to the handle and ready for use in a scraping procedure.

The stud on the blade preferably has a slight friction fit into the hole and the handle to hold the blade adjacent the handle. This friction fit can include a spring loaded circular snap ring or other retainer residing in a circumferential groove near a base tip of the stud. The retainer "snaps" past the hole in the handle to hold the blade to the handle. Alternatively, the stud may have structure which cooperatively engages moveable structure within the handle. For example, the stud may include a through-hole or grooves on the sides, and the handle may include a post or yoke that may be inserted into the hole or grooves, respectively. The post or yoke may be remotely controlled by a knob located on the proximal end of the handle. The post or yoke would preferably be biased in a forward, locking position, and pulling on the knob would retract the post or yoke, thereby unlocking the blade. The knob may also require rotation prior to pulling so that the knob cannot be accidentally pulled during use. In such an embodiment, the stud need not pass through the handle. In addition, the hole for receiving the stud need not extend through the handle.

To remove the blade, the distal end of the handle can be struck on a hard surface causing a base tip of the stud to strike the surface and drive this stud up through the hole, releasing the blade from the handle. In an alternative embodiment, pulling, or rotating and then pulling, the release knob release the blade from the handle. The blade can be disposed of (or conceivably sterilized, resharpened and reused). With the blade being disposable, the handle can be readily sterilized, such as through autoclave or chemclave procedures, and is then ready to receive a new blade (or a refurbished, sharpened or otherwise rehabilitated or previously used blade) for reuse of the handle with another blade in a surgical procedure which requires scraping.

The invention also includes a container for at least one, and optionally a set of, scrapers. In one embodiment, this container includes a lower tray with holes to facilitate sterilization. The tray has perimeter sides with two shorter sides having handles. A handle support is preferably provided which is configured to either capture the scraper proximal end therein, or to allow the scraper proximal end to rest freely thereon, depending on if secure containment, or ease of grasping for use, is to be emphasized. The handle support has a top shelf with pockets beneath to either hold the scraper handle securely or present the handle end for grasping. A cover tray is also provided which can nest under the lower tray when not in use and can cover the lower tray when in use, the cover having saddles and a handle slit to fit with the lower tray handles in either configuration. The container also has structure to hold extra blades in an orientation that would permit the user to attach a new blade to the handle without touching the handle, such as for example, holding the extra blades so that the proximal end of the blade and the stud are exposed.

OBJECTS OF THE INVENTION

Accordingly, a primary feature of the present invention is to provide a surgical scraper which can have a new sharp blade.

Another feature of the present invention is to provide a surgical scraper which can easily have a blade attached, removed and reattached, so that one blade can be replaced with another blade having a more preferred size, sharpness, state of sterilization, or other characteristics.

Another feature of the present invention is to provide a method for attaching and removing a blade from a surgical scraper which is easy to perform, without grasping the blade.

Another feature of the present invention is to provide a method for using a scraper in a surgical procedure with a blade of the scraper initially provided separate from the scraper.

Another feature of the present invention is to provide a surgical scraper with a removable blade that has the blade held securely to the scraper and without movement relative to the scraper during scraping procedures, but which can be readily removed when desired.

Another feature of the present invention is to provide a scraper with a separate blade which can all be sterilized, either together or separately.

Another feature of the present invention is to provide a container for surgical scrapers which can itself be sterilized and can contain the scrapers during a sterilization procedure for the scrapers, with the container configured to hold the scrapers securely therein in a first position and allow the scrapers to be readily grasped and used when in a second position.

Other features of the present invention will become apparent from a study of the included figures, claims and detailed description of the invention.

BRIEF DESCRIPTION OF THE DRAWINGS

FIG. 1 is a perspective view of a surgical scraper according to the prior art.

FIG. 2 is a perspective detail of a distal end of the prior art surgical scraper of FIG. 1.

FIG. 3 is a perspective view of the surgical scraper of this invention, without a blade thereon.

FIG. 4 is a detailed view of a distal end of the surgical scraper of this invention with a blade exploded away from the distal end and revealing how the blade is attached to the distal end of the scraper.

FIG. 5 is a top plan view of the distal end of the scraper of this invention, without the blade thereon.

DESCRIPTION OF THE PREFERRED EMBODIMENT

Figure 6:
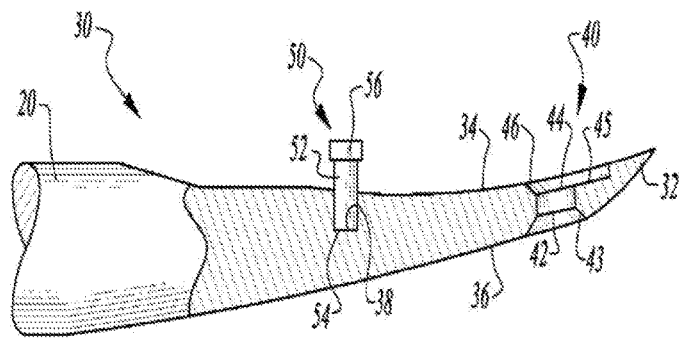
FIG. 6 is a side elevation partial sectional view of the distal end of the scraper of this invention, without the blade thereon.
Figure 7:
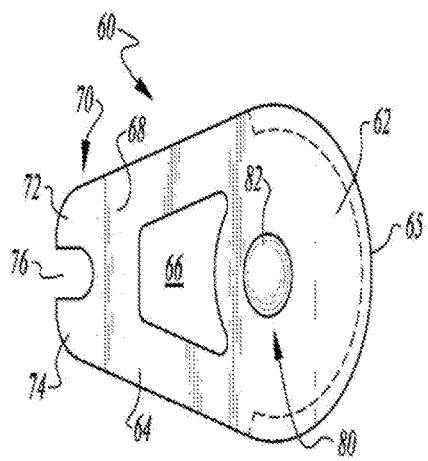
FIG. 7 is a top plan view of an exemplary scraper blade for attachment to the scraper according to this invention.

Referring to the drawings, wherein like reference numerals represent like parts throughout the various drawing figures, reference numeral 10 is directed to a scraper (FIGS. 3, 4 and 10) which, in the preferred form, is a surgical scraper for use in various surgical procedures, such as where bone needs to be scraped of tissue. The scraper 10 includes a removable blade 60 so that the scraper 10 can be routinely fitted with a new sharpened blade 60 and be ready for use with a sharp cutting edge 65.

The scraper 10 is in many ways similar to a prior art scraper S (FIGS. 1 and 2) which is also often referred to as a "Cobb Elevator." The prior art scraper S includes a tip T extending from a handle H by an arm A. The tip includes a face F which is flattened and preferably, although not necessarily, slightly concave. The tip T is sharpened and used for scraping. With this invention, the existing scraper S is modified so that a removable blade 60 (FIGS. 4 and 7-10) can be removably attached to a distal end 30 of the scraper 10 whenever desired.

In essence, and with particular reference to FIGS. 3 and 4, basic details of the scraper 10 are described according to this preferred embodiment. The scraper 10 includes an arm 20 extending to a distal end 30. The distal end 30 includes at least a portion of a fastener thereon which is used to removably attach the blade 60 to the distal end 30 of the scraper 10. The fastener in this preferred embodiment includes a hole 40 passing through the distal end 30 of the scraper 10 as well as a pin 50 extending from the distal end 30 of the scraper 10. The blade 60 has a cutting edge 65 at an edge thereof which extends slightly beyond the distal end 30 of the scraper 10, so that the cutting edge 65 can come into contact with structures to be scraped, such as bone surfaces. The blade 60 includes a yoke 70 which can interact with the pin 50 to retain the blade 60 at the distal end 30 of the scraper 10. The blade 60 also includes a stud 80 extending from the blade 60. The stud 80 is sized to pass through the hole 40 and to further assist in retaining the blade 60 in a removably attachable fashion to the distal end 30 of the scraper 10. A container 110 is also disclosed (FIGS. 10-14) which includes a lower tray 120 and cover tray 150 which can act together to support and contain scrapers 10 therein.

More specifically, and with particular reference to FIG. 3, basic details of the scraper 10, apart from the distal end 30, are described, according to a most preferred embodiment. The scraper 10 includes a proximal end 12 opposite the distal end 30. The scraper 10 has a generally elongate rigid body preferably formed of a unitary mass of material, typically a surgical stainless steel. As an alternative, this elongate rigid body could be formed of separate parts joined together.

The proximal end 12 includes a handle 14 thereon configured to be readily gripped by a hand of a user. A rounded end 16 defines a portion of the proximal end 12 most distant from the distal end 30. A neck 18 defines a portion of a handle 14 most distant from the rounded end 16 at which the handle 14 transitions into an arm 20. This arm 20 is preferably cylindrical (as is also the handle 14) but with a smaller diameter than that of the handle 14. The arm 20 extends to the distal end 30.

The handle 14 can be fitted with knurling or other surface roughening or ribbing to enhance frictional engagement of the handle 14 by a hand of a user, often a surgeon wearing gloves. These portions of the scraper 10 away from the distal end 30 are in this preferred embodiment similar to corresponding details of the prior art scraper S (FIG. 1). These details could be altered to match other prior art scrapers, or scrapers developed in the future, to achieve the basic function of allowing the scraper 10 to be securely held and handled by a surgeon or other medical professional.

With particular reference to FIGS. 3-9, details of the distal end 30 of the scraper 10 are described, according to this most preferred embodiment. The distal end 30 has a tip 32 defining a portion of the distal end 30 most distant from the proximal end 12. This distal end 30 also includes a concave face 34 opposite a rear surface 36. While it is conceivable that the concave face 34 could be flat, preferably it is slightly concave and matching somewhat a concave curving nature of the blade 60. However, the concave face 34 preferably is not as sharply curved as is the blade 60. This helps to ensure that the blade 60 remains in contact with the concave face 34 when the blade 60 is actually bent slightly to allow it to attach to the distal end 30 of the scraper 10. With the blade 60 so pre-stressed and pressing against the concave face 34 of the distal end 30, the blade 30 does not move relative to the distal end 30 of the scraper 10 and is securely held in place even when significant loads are applied between the scraper 10 and a structure being scraped.

The tip 32 preferably extends a sufficient distance so that the tip 32 can support substantially all of the blade 60 all the way to the cutting edge 65, but stopping short so that the cutting edge 65 of the blade 60 can extend slightly past the tip 32 of the distal end 30. A bore 38 is preferably provided on a portion of the distal end 30 closer to the arm 20 from which the distal end 30 extends. This bore 38 is preferably a blind bore into which the pin 50 can be mounted. As an alternative, this pin 50 structure could be cast or otherwise formed integrally with other portions of the scraper 10. In another embodiment, the bore 38 may be an open bore that extends from the concave face 34 to the rear surface 36 of the distal end 30. In such embodiment, pin 50 may extend throughout the length of the open bore. A nut or other fastener may be provided on the bottom of the scraper 10 so as to fix pin 50 to the scraper 10.

The hole 40 provides one portion of a fastener to hold the blade 60 to the distal end 30, along with the pin 50. As an option, the blade could be held in place by the hole 40 alone, or by multiple holes 40 receiving multiple studs 80. In the preferred embodiment, the hole 40 passes entirely from the concave face 34 to the rear surface 36 of the distal end 30. This hole 40 is configured to receive the stud 80 of the blade 60 passing therethrough in a removably attachable fashion. This hole 40 preferably is circular in cross-section and extends from a lower end 42 adjacent the rear surface 36 to an upper end 44 adjacent the concave face 34.

Preferably, a beveled collar 43 surrounds the lower end 42 of the hole 40. This beveled collar 43 slightly increases a diameter of the hole 40 adjacent the lower end 42. The hole 40 has a diameter at the lower end 42 slightly greater than a diameter of the stud 80 but slightly less than a diameter of the snap ring 88 or other retainer. However, the beveled collar 43 expands this diameter of the hole 40 adjacent the lower end 42 to be slightly greater than a diameter of the snap ring 88 or other retainer, at least when this snap ring 88 is compressed somewhat. The beveled collar 43 thus provides a location where the snap ring 88 can reside when the stud 80 is securely held within the hole 40.

Figure 9:
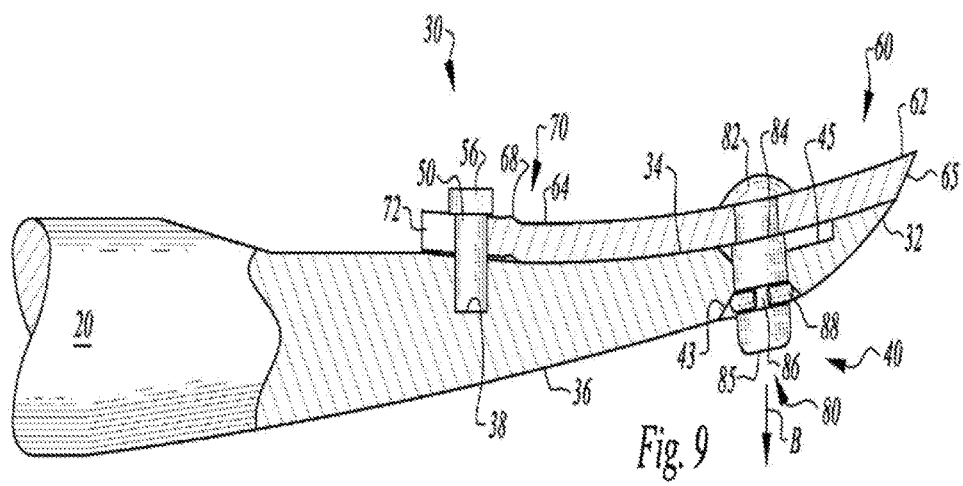
FIG. 9 is a side elevation view of the distal end of the scraper and the blade shown attached together in a partial cut away view.

Because the beveled collar 43 exhibits a bit of a ramp, the stud 80 along with its associated blade 60 can be removed from the hole 40 when an appropriately high force is applied to the stud 80 (such as by striking or pressing the base tip 85 of the stud 80 against a hard surface (along arrow B of FIG. 9). This striking force allows the stud 80 and associated blade 60 to pop out of the hole 40 and to allow the blade 60 to be removed from the scraper 10. A steady force on the base tip 85 of the stud 80 is also effective in releasing the stud 80 and associated blade 40 from the distal end 30. Alternatively, instead of the beveled collar 43, hole 40 may include an interior groove (not shown). In such an embodiment, snap ring 88 is provided at a location further from the base tip 85 so as to communicate with the interior groove. In such manner, snap ring 88 does not exit scraper 10, but resides therein while blade 60 is installed on scraper 10. Removal of blade 60 may occur in similar fashion to that described above.

At the upper end 44, a beveled edge 46 is also preferably provided on one side thereof. On a side of the upper end 44 closest to the tip 32, a forward recess 45 is provided. This forward recess 45 is larger than the beveled edge 46 and extends only in a forward direction toward the tip 32. A depth of this forward recess 45 is only a portion of the thickness of the distal end 32. The forward recess 45 is sufficiently large so that the base tip 85 of the stud 80 can initially pass at least partially into this forward recess 45 (arrow D of FIG. 4) as the yoke 70 is being aligned with the pin 50, before the base tip 85 of the stud 80 transitions into passing through the hole 40 and snapping securely into the hole 40, so that the blade 60 is held tightly against the concave face 34 of the distal end 30 of the scraper 10. Alternatively, in embodiments where hole 40 and tip 50 are reversed (i.e., hole 40 is located distal to tip 32 and pin 50 is located proximal to tip 32), a rear recess may be provided. Such rear recess would function in substantially the same manner as the front recess 45 described above.

The pin 50 preferably provides a further portion of the fastener on the distal end 30 of the scraper 10. This pin 50 preferably extends up from the concave face 34 along a post 52 ending at a cap 56 defining an uppermost portion of the pin 50. A root 54 defines an end of the post 52 opposite the cap 56. This root 54 is buried deep into the bore 38 and preferably exhibits a press fit or is otherwise bonded within the bore 38 or otherwise fastened so that the pin 50 is affixed to the distal end 30 within the bore 38. In an alternative embodiment, pin 50 is formed integrally with scraper 10 such that bore 38 and root 54 are not provided.

The cap 56 is spaced from the concave face 34 by a distance similar to a thickness of the blade 60, especially portions of the blade 60 adjacent the yoke 70. In this way, the yoke 70 can fit under the cap 56 and be secured to the pin 50 as at least a portion of the fastener of this invention for fastening the blade 60 to the scraper 10 in a removably attachable fashion.

In particular, the post 52 preferably has a circular cross-section and a diameter no greater than, and preferably slightly less than, a width of a slot 76 in the yoke 70. The yoke 70 (FIGS. 4 and 7) is located at a proximal side 62 of the blade 60, opposite the cutting edge 65. This yoke 70 includes a slot 76 at a mid-portion thereof and with a left ear 72 and right ear 74 on opposite sides of this slot 76. By sizing the posts 52 to be smaller than a width of the slot 76, between the left ear 72 and right ear 74, the slot 76 can receive the post 52 of the pin 50 therein when the yoke 70 is brought adjacent the pin 50 (along arrow C of FIG. 4). By keeping a thickness of the blade 60 adjacent the yoke 70 less than a height of the cap 56 above the concave face 34, this yoke 70 can fully fit under the cap 54 and adjacent the post 52 to most securely hold the blade 60 to the scraper 10. In an alternative embodiment, slot 76 may be sized to have a slightly smaller circular cross-section and diameter than post 52. Yoke 70 may then be affixed to pin 50 via interference or pressure fit. Similarly, pin 50 may be provided without cap 56.

With particular reference to FIGS. 4 and 7-9, particular details of the blade 60 are described, according to this most preferred embodiment. The blade 60 is preferably formed of stainless steel, although other materials such as plastics for example, are clearly envisioned, and is a thin plate exhibiting sufficient resilience to allow it to be bent somewhat and be biased toward returning to its original shape. The blade 60 has a proximal side 62 opposite a distal side 64, with a cutting edge 65 at the distal side 64. This edge 65 is sharper than that of prior art scrapers and capable of scraping in two directions, so that the surgeon is less often required to change hand positions. The blade 60 preferably includes a relief opening 66, especially for larger sizes of the blade 60, to further facilitate flexing of the blade 60 and without warping thereof.

A step 68 is preferably provided adjacent the proximal side 62 and before the yoke 70. This step 68 elevates the yoke 70 slightly relative to other portions of the blade 60 and helps to securely press the blade 60 against the concave face 34 of the distal end 30 of the scraper 10, when the blade 60 is installed onto the scraper 10. While the step 68 is shown with portions of the blade 60 on either side of the step 68 generally parallel with each other, it is conceivable that this step 68 would instead be a form of flare where the ears 72, 74 of the yoke 70 would be angled upward and either not bent back downward or only bent back downward partially after the step 68. Alternatively, blade 60 may be provided absent the step 68.

The blade 60 preferably includes the stud 80 affixed thereto as a portion of the fastener of this invention. As an alternative, the blade 60 could be studless and captured by other structures either on the distal end 30, on the blade 60 or both. It is also conceivable that the blade 60 could have more than one stud 80. This stud 80 could be formed along with the blade 60 (i.e., formed integrally with the blade 60), but may be attached through a hole in the blade 60. This stud 80 includes a crown 82 on an upper side of the blade 60. Alternatively, stud 80 may be provided absent crown 82. A shaft 84 extends through the hole in the blade 60 and away from the crown 82, terminating at the base tip 85. The shaft 84 extends along a centerline substantially perpendicular to a plane tangent to the blade 60 at the hole in the stud 80. The shaft 84 can include a step therein to securely hold the stud 80 relative to the blade 60, and sandwiching portions of the blade 60 between the crown 82 and this step in the shaft 84.

The stud 80 includes a groove 86 extending circumferentially at a location on the shaft 84 somewhat closer to the base tip 85 than to the crown 82. This distance that the groove 86 is located away from the blade 60 is selected to be similar to a height of the hole 40 in the distal end 30 of the scraper 10, so that a snap ring 88 residing within the groove 86 can pass entirely through the hole 40 and at least into the beveled edge 43 portion of the hole 40, so that the stud 80 passes entirely through the hole 40 and securely holds the blade 60 to the distal end 30 of the scraper 10. Alternatively, groove 86 may be positioned more distal to base tip 85 such that groove 86 does not extend into beveled edge 43.

The snap ring 88 is preferably just shy of one full turn of a helical compression spring. This ring is formed of a spring steel and is highly resilient, however, a resilient plastic ring or any other configuration or material known in the art may be used. The snap ring 88 is also sized to be slightly larger in diameter than the shaft 84 at its outer diameter but slightly less than a diameter of the shaft 84 at an inner diameter so that the snap ring 88 is held within the groove 86 but extends outward somewhat. A sufficient clearance is provided within the groove 86 at ends of the snap ring 88 so that the snap ring 88 can be compressed and caused to extend radially outward less, or even to reside entirely within the groove 86. By forming the snap ring 88 from a portion of a helical spring, the groove 86 can have a height along a central axis of the stud 80 which is slightly greater than a diameter of this snap ring cross-section, and the snap ring 88 still holds tightly within the groove, providing a highly reliable and repeatable snapping action for snapping the stud 80 of the blade 60 into the hole 40 to secure the blade 60 to the scraper 10, but also allow removal. Alternatively, snap ring 88 may be formed integrally with and as a protrusion on stud 80 provided that snap ring 88 can still deform as needed.

When installing the blade, the particular procedure to be followed (FIG. 4) involves first bringing the blade 60 proximate to and overlying the concave face 34 of the distal end 30 (FIG. 4). Next, the yoke 70 is positioned to receive the pin 50 therein, by sliding of the blade 60 horizontally (along arrow C of FIG. 4). This motion of the yoke 70 under the cap 56 of the pin 50 involves the blade 60 being angled somewhat because the stud 80 has not begun to go into the hole 40 yet. Further motion of the blade 60 with the yoke 70 beginning to engage the pin 50 involves the blade 60 beginning to rotate downward and translate (along arrow E of FIG. 4).

The base tip 85 of the stud 80 initially passes into the forward recess 45 of the hole 40. Finally, when the slot 76 of the yoke 70 has fully engaged the post 52 of the pin 50, the stud 80 is clear to pass vertically down through the hole 40 (along arrow D of FIG. 4). This translation continues until the snap ring 88 reaches at least the beveled collar 43 at the lower end 42 of the hole 40 (FIG. 9). The blade 60 is now securely held adjacent the distal end 30 and is ready for scraping. Because the blade 60 includes a slightly greater curvature than the concave face 34, the blade 60 is pre-stressed when fully attached as described above, and immobile relative to the distal end 30 of the scraper 10, giving the surgeon or other medical professional good performance and feedback during use of the scraper 10.

To remove the blade 60, a user can strike the base tip 85 of the stud 80 against a hard surface (along arrow B of FIG. 9). A somewhat quick and low force striking motion will compress the snap ring 88 sufficiently so that the stud 80 can translate upward and out of the hole 40, and then the yoke 70 can release the pin 50 so that the blade 60 is released. Beneficially, this removal process does not involve a user ever having to handle the blade 60. The blade 60 has the sharp cutting edge 65 and has typically been contaminated with bodily fluids and other bodily materials during use, making handling of the blade 60 a hazardous procedure best avoided. As an alternative, a slower but steady pressure can be provided between the base tip 85 and an underlying hard surface (or even pushing against a user's hand) until the snap ring 88 has compressed sufficiently to allow the stud 80 to translate upwards and for the blade 60 to be removed from the scraper 10.

Figure 8:
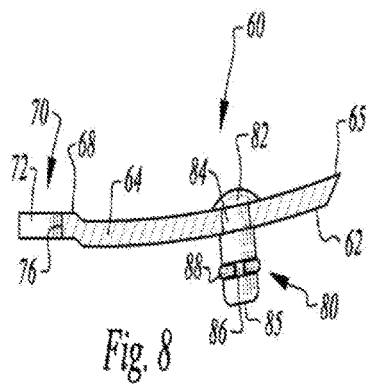
FIG. 8 is a side elevation full sectional view of the scraper blade of FIG. 7.
Figure 8A:
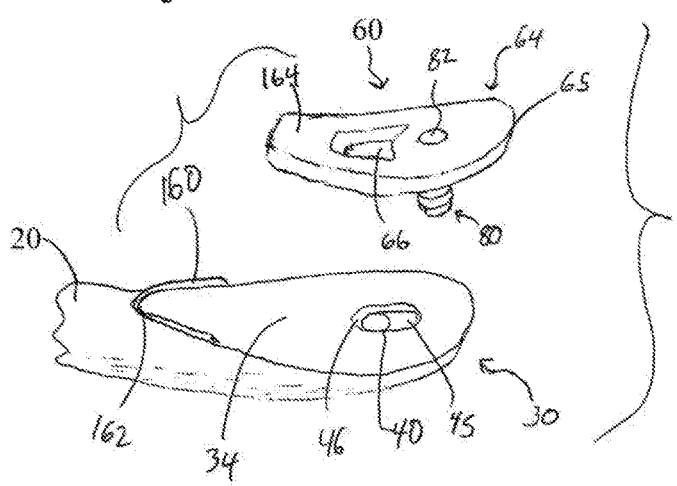
FIG. 8A is a perspective exploded view of a distal end of a surgical scraper according to an embodiment of the present invention.

It should be understood that various modifications and alternate embodiments may be made to the described scraper 10 without departing from the scope of the invention. For example, with reference to FIG. 8A, a protrusion 160 may be provided at the proximal end of distal end 30 along an edge 162 of the concave face 34. The protrusion 160 extends substantially perpendicularly to the edge 162 of concave face 34. The protrusion 160 may take the place of the combination of pin 50 and yoke 70 and function similarly thereto such that it may retain the blade 60 while blade 60 is being installed on distal end 30 of scraper 10. The protrusion 160 preferably has a thickness substantially equivalent to the thickness of blade 60, but may also be provided with more or less thickness. In order for blade 60 to communicate with protrusion 160, blade 60 extends into a proximal region 164 instead of yoke 70. Proximal region 164 of blade 60 extends in the same plane as blade 60 and is substantially similar thereto.

Figure 8B:
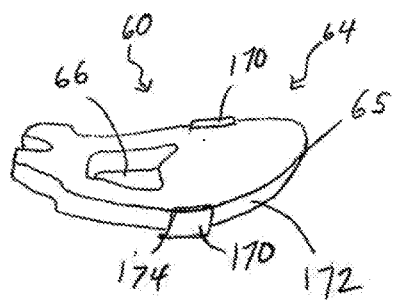
FIG. 8B is a perspective view of a scraper blade according to an embodiment of the present invention.
Figure 8C:
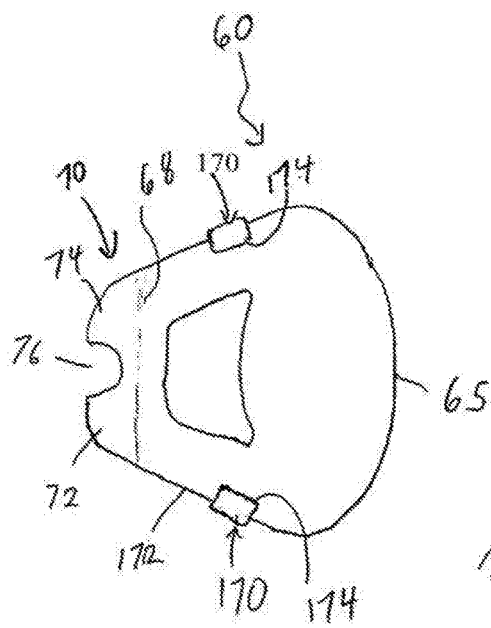
FIG. 8C is a bottom view of the scraper blade of FIG. 8B.
Figure 8D:
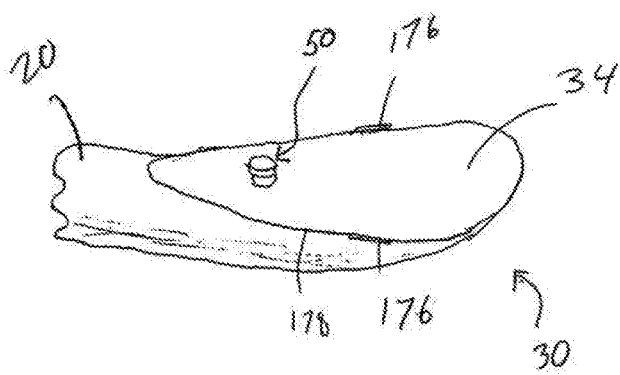
FIG. 8D is a perspective view of a distal end of a surgical scraper according to an embodiment of the present invention.

Similarly, various other structures may be provided to substitute for stud 80. With reference to FIGS. 8B-8D, one such structure is depicted. Clip members 170 may be provided along the lateral sides 172 of blade 60. The clip members 170 have hook portions 174 that extend a distance into the plane of the blade 60. Hook portions 174 are provided with a thickness preferably substantially similar to the thickness of concave face 34 such that clip members 170 may be pressure fit or "snapped" onto distal end 30 of scraper 10. In some embodiments, protrusions 176 may be provided on the lateral sides 178 of distal end 30 of scraper 10 to improve fixation between blade 60 and scraper 10. The embodiment depicted in FIGS. 8B-8D may employ a stud 80 and corresponding hole 40 as described above, however, stud 80 and corresponding hole 40 are not necessarily present.

In such embodiment, removal of blade 60 may be effectuated by striking distal side 64 of blade 60 against a hard surface in a substantially similar manner to that described with reference to stud 80 above. Removal may also be effectuated by physically manipulating clip members 170 to actuate their release of distal end 30 of scraper 10.

Figure 10:
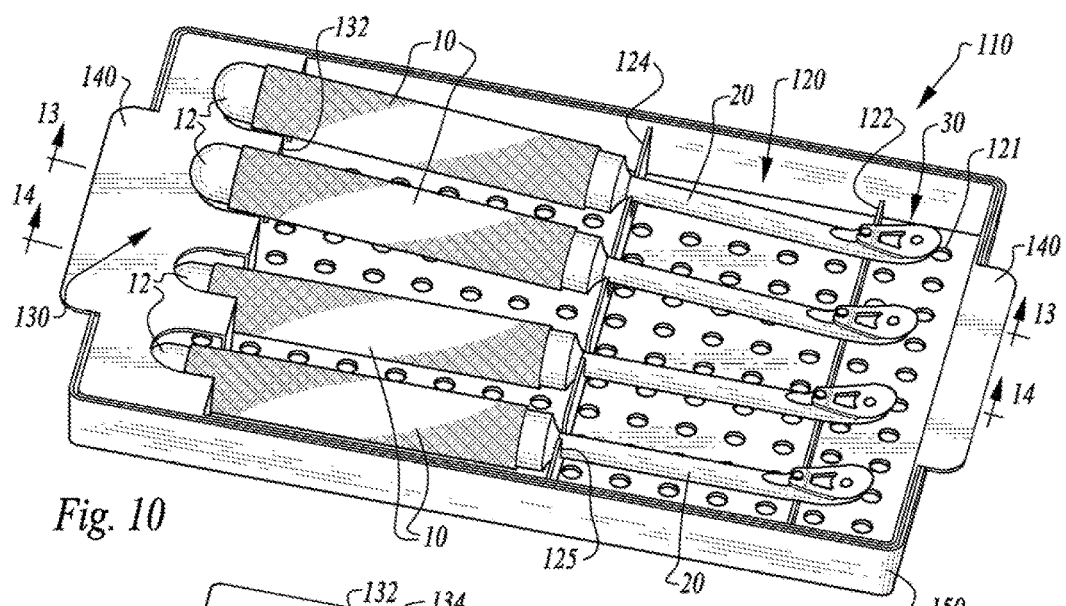
FIG. 10 is a perspective view of a container of this invention for holding surgical scrapers with a cover tray of the container inverted and nested under a lower tray of the container.
Figure 11:
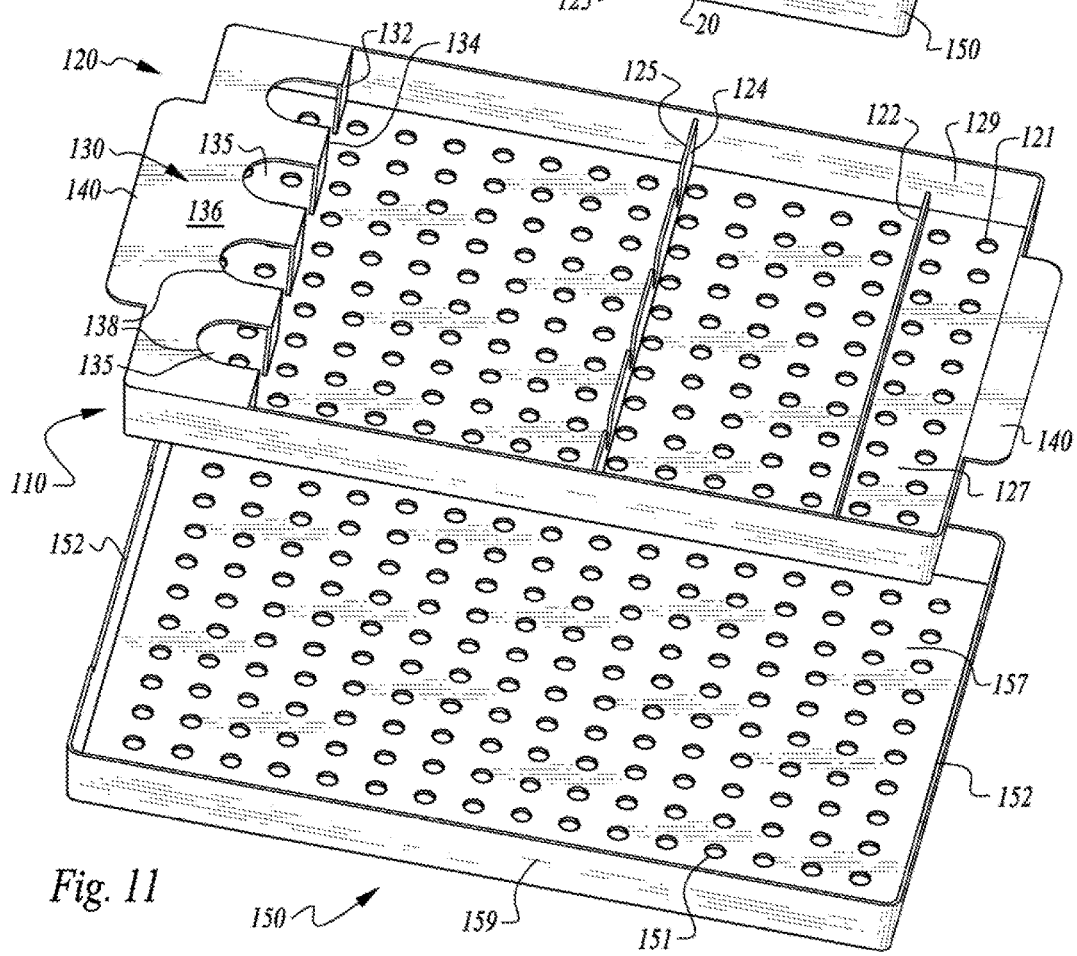
FIG. 11 is a perspective view similar to that which is shown in FIG. 10 but with the lower tray and cover tray exploded away from each other.
Figure 12:
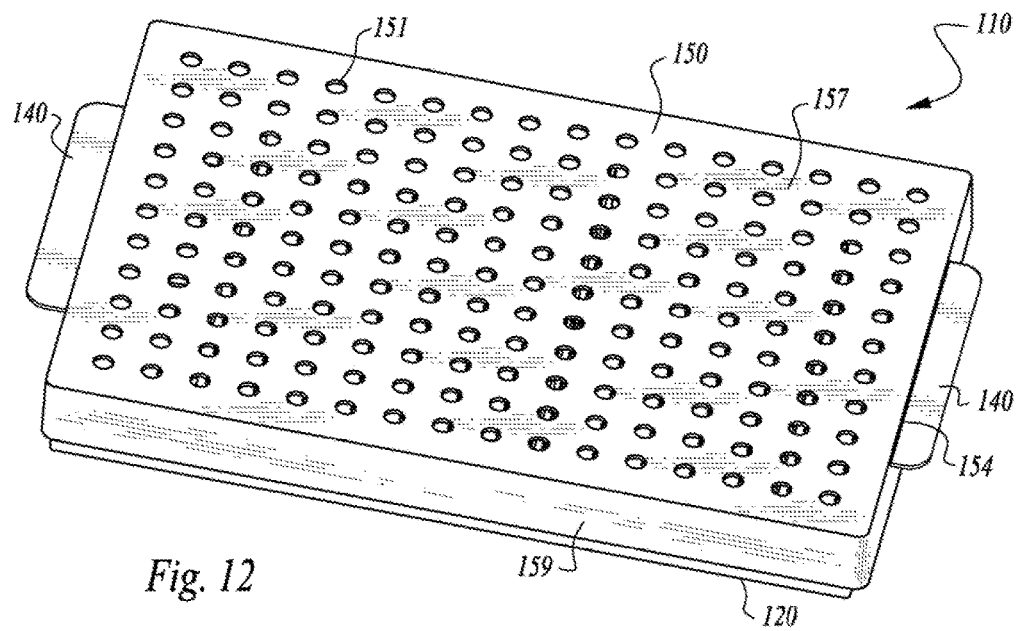
FIG. 12 is a perspective view similar to that which is shown in FIG. 10, but with the cover tray inverted and attached over the lower tray to fully contain surgical scrapers therein.
Figure 13:
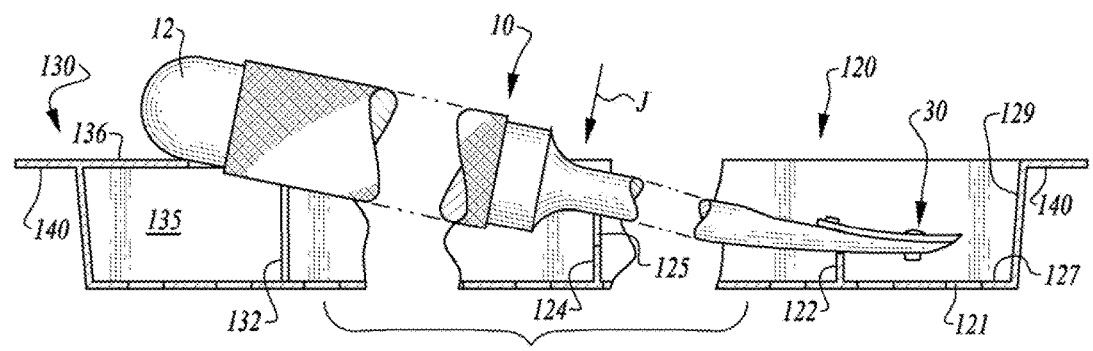
FIG. 13 is a full sectional front elevation view of the lower tray of the container of this invention with a scraper shown in an elevated, ready to use position, the view taken along line 13-13 of FIG. 10.
Figure 14:
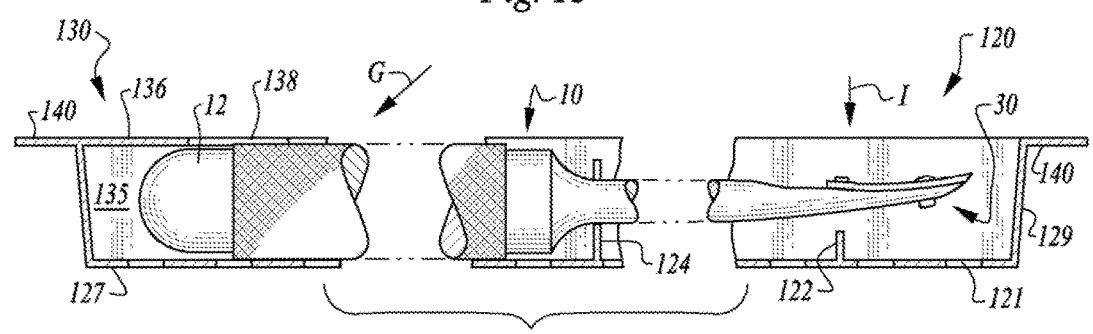
FIG. 14 is a full sectional front elevation view of the lower tray of the container of this invention with a scraper shown in a captured orientation for secure storage within the container, the view taken along line 14-14 of FIG. 10.

With particular reference to FIGS. 10-14, details of the container 110 for housing the scraper 10, are described according to a preferred embodiment. The container 110 holds the scraper 10 in at least two positions including either a ready position where the scraper 10 is ready to be grasped and used (FIGS. 10 and 13) or a securely stored position where the scraper 10 resists removal from the container 110 (FIGS. 10 and 14). The container 110 includes a lower tray 120 and a cover tray 150. The lower tray 120 and cover tray 150 each include a plurality of holes 121, 151 passing therethrough so that steam or other sterilizing fluids can readily pass through the container 110 for sterilizing of scrapers 10 contained therein. The scrapers 10 can include blades 60 on distal ends 30 thereof or the blades 60 can be stored separately or stored within the container 110, but not attached to the scrapers 10.

The lower tray 120 generally includes a floor 127 with perimeter sides 129 extending up from the floor 127. A head rest 122 is in the form of a rib extending vertically up from the floor 127. A neck rest 124 defines a second rib extending up from the floor 127, parallel to the head rest 122. The neck rest 124 includes a series of cradles 125 therein with each of the cradles 125 sized to receive an arm 20 portion of the scraper 10 thereon (FIG. 10). One end of the lower tray 120 includes a handle support 130 therein. This handle support 130 supports the handle 30 of a scraper 10 either resting thereon (FIG. 13) or stored therein (FIG. 14).

The handle support 130 includes vertical spacer walls 132 that space multiple scrapers away from each other. Pathways 134 are provided between these spacer walls 132 which extend laterally into pockets 135 beneath a top shelf 136 of the handle support 130. Notches 138 are provided in the top shelf 136 aligned with the pathways 134. The notches 138 are large enough along with the pathways 134 in the pockets 135 so that if the proximal end 12 of a scraper 10 is brought down into the pockets 135 in a somewhat down and then lateral motion (along arrow G of FIG. 14), the proximal end 12 can be tucked into the pocket 135 and be securely held within the pocket 135, unless a reverse action is utilized to remove the scraper 10.

When in this stored position (FIG. 14), the arm 20 rests upon the neck rest 124 within one of the cradles 125. The distal end 30 is up off of the headrest 122 and in free space so that all surfaces of the distal end 30 can be fully sterilized and kept sterile. After initial angled placement of the proximal end 12 into the pocket 135 (along arrow G of FIG. 14), the scraper 10 is further rotated downward into a horizontal orientation (along arrow I of FIG. 14) until it is fully contained within the lower tray 110.

If it is desirable to have the scraper 10 ready to be quickly grasped and used, the scraper 10 can be merely lowered vertically downward (along arrow J of FIG. 13). The proximal end 12 will impact the top shelf 136 of the handle support 130 and remain outside of the pockets 135 and extend only partially into one of the notches 138 and upper portions of one of the pathways 134 between adjacent spacer walls 132. In this ready-to-use orientation, the distal end 30 is generally resting upon the headrest 122. Such a scraper 10 oriented as shown in FIG. 13, is ready to be quickly grasped and used without any special removal technique being required. Alternatively, distal end 30 may be positioned in any orientation that facilitates easy removal prior to use.

Handles 140 extend from ends of the lower tray 120. The handles 140 preferably vary in size to interact with corresponding features of the cover tray 150 most effectively. Alternatively, the lower tray 120 may be provided without handles 140.

The cover tray 150 has a general form similar to that of the lower tray 120 but slightly larger so that the two can nest together. In particular, the cover tray 150 includes a floor 157 with perimeter sides 159 extending up from the floor 157, and with a plurality of holes 151 in the floor 157. In one embodiment, the cover tray 150 does not have handles. However, cover tray 150 may be provided with handles, if desired. To allow full nesting, the end perimeter sides of the cover tray 150 include handle saddles 152 formed therein (FIG. 11) so that the handles 140 of the lower tray 120 can extend through these saddles 152 when the lower tray 120 is resting on top of the cover tray 150. By making these saddles 152 of differing sizes matching sizes of the handles 140 of the opposing ends of the lower tray 120, an orientation of the cover tray 150 relative to the lower tray 120 can be maintained. This nested open configuration for the container 110 is depicted in FIG. 10.

When it is desired to close the container 110, the cover tray 150 is removed from beneath the lower tray 120, inverted, and then placed over the lower tray 120. Preferably, a handle slit 154 is provided at an end of the cover tray 150 adjacent a handle 140 of the lower tray 120 opposite the handle support 130. This slit is at a junction of the floor 157 and the perimeter 159. A handle 140 of the lower tray 120 passes through this handle slit 154, so that the end of the container 110 opposite the handle support 130 is securely held to the cover tray 150. Displacement of the cover tray 150 away from the lower tray 120 is thus discouraged. With one end of the cover tray 150 securely held to the lower tray 120, and with the other end of the lower tray 120 having the handle support 130 for securely holding the scraper 10 therein, the overall container 110 securely holds the scrapers 10 therein without allowing significant movement, even if the container 110 is handled roughly.

Having thus described the invention in this way, it should be apparent that various different modifications can be made to the preferred and other embodiments without departing from the scope and spirit of this invention disclosure. When structures are identified as a means to perform a function, the identification is intended to include all structures, and their equivalents, which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A surgical scraper, the scraper comprising:
    an elongate rigid body extending between a proximal end and a distal end, the proximal end including a handle adapted to be gripped by a hand of a user;
    a head located at the distal end, the head including a pin and a hole, and
    a blade of thin form having a proximal side, a distal side opposite the proximal side and having a cutting edge thereon, the blade having a slot and a stud, wherein the slot is configured to receive the pin therein and the stud is configured to be inserted into the hole;
    wherein the slot and the pin cooperate and the stud and the hole cooperate to hold the blade on the head of the scraper; and
    wherein the blade includes a yoke on the proximal side, the yoke including the slot therein, the pin having a cap thereon, the cap spaced from the face of the head of the scraper, the space being at least as great as a thickness of the blade at the yoke.

2. The scraper of claim 1, wherein a step is provided in the blade between the yoke and the distal side of the blade, the step causing the yoke to be elevated above portions of the blade on a side of the step opposite the yoke.

3. The scraper of claim 2, wherein the stud includes a groove on a portion of the stud below the thin form of the blade, a retainer having at least a portion thereof located within the groove and at least a portion thereof extending out of the groove, the hole in the head of the scraper having a beveled edge, the hole at least as long as a distance that the groove is spaced away from the thin form of the blade, such that the retainer can reside at least partially outside of the hole when the stud is located through the hole.

4. The scraper of claim 3, wherein an upper end of the hole opposite the lower end includes a forward recess extending toward the distal end of the scraper.

5. A method of for scraping bodily structures during surgery, the method comprising:
    identifying a scraper having an elongate rigid body extending between a proximal end and a distal end, the proximal end including a handle adapted to be gripped by a hand of a user, the distal end including a head, the head including a pin and a hole, a first blade of thin form having a distal side with a cutting edge thereon, the first blade having a slot and a stud, wherein the slot is configured to receive the pin therein and the stud is configured to be inserted into the hole;
    attaching the first blade to the distal end of the elongate rigid body of the scraper;
    scraping a bodily structure with the cutting edge of the first blade;
    striking the distal end of the scraper against a hard surface to remove the first blade;
    removing the first blade from the head of the scraper; and
    attaching a second blade to the head of the scraper.

6. The method of claim 5, wherein the identifying step includes the pin fitting within the slot to at least partially hold the first blade to the head, the stud extending non-parallel with a plane tangent to the thin form of the first blade, the stud sized to fit within the hole to at least partially hold the first blade to the head of the scraper, the stud having a base tip extending out past a rear surface of the scraper.

7. The method of claim 6, wherein the attaching step includes:
    passing the base tip into a forward recess, then into the hole until the retainer extends at least partially out of the lower end of the hole.

* * * * *